US010245097B2

(12) United States Patent
Honda et al.

(10) Patent No.: US 10,245,097 B2
(45) Date of Patent: Apr. 2, 2019

(54) LIVING TISSUE BONDING SYSTEM AND METHOD FOR OPERATING LIVING TISSUE BONDING SYSTEM

(71) Applicant: OLYMPUS CORPORATION, Tokyo (JP)

(72) Inventors: Yoshitaka Honda, Hachioji (JP); Takashi Irisawa, Hachioji (JP); Kazue Tanaka, Sagamihara (JP); Sadayoshi Takami, Hachioji (JP); Toshifumi Katsuragi, Hachioji (JP); Hiroko Sakamoto, Tokyo (JP); Satomi Sakao, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 178 days.

(21) Appl. No.: 15/012,537

(22) Filed: Feb. 1, 2016

(65) Prior Publication Data
US 2016/0143684 A1 May 26, 2016

Related U.S. Application Data

(63) Continuation of application No. PCT/JP2014/070348, filed on Aug. 1, 2014.
(Continued)

(51) Int. Cl.
A61B 18/08 (2006.01)
A61B 18/14 (2006.01)
A61B 18/00 (2006.01)

(52) U.S. Cl.
CPC ........ A61B 18/085 (2013.01); A61B 18/1445 (2013.01); A61B 2018/0063 (2013.01);
(Continued)

(58) Field of Classification Search
CPC ........... A61B 2018/00571; A61B 2018/00589; A61B 2018/00619; A61B 2018/0063;
(Continued)

(56) References Cited

U.S. PATENT DOCUMENTS 5,553,622 A 9/1996 McKown et al.
6,626,901 B1 9/2003 Treat et al.
(Continued)

FOREIGN PATENT DOCUMENTS

EP 2106762 A1 10/2009
JP 2001-514541 A 9/2001
(Continued)

OTHER PUBLICATIONS

Feb. 22, 2017 Extended European Search Report issued in Patent Application No. 14833046.7.
(Continued)

Primary Examiner — Ahmed Farah
(74) Attorney, Agent, or Firm — Oliff PLC

(57) ABSTRACT

A living tissue bonding system including: a sandwiching section for sandwiching living tissue; a power source for supplying to the living tissue treatment energy for bonding the living tissue sandwiched by the sandwiching section; a temperature measuring section for measuring a temperature of the living tissue sandwiched by the sandwiching section; a calculation section calculating, from the temperature of the living tissue measured by the temperature measuring section and a time period of applying the treatment energy, a time integral value of the temperature of the living tissue; a comparison section comparing the time integral value of the temperature of the living tissue calculated by the calculation section with a predetermined setting value; and an instruction section giving an instruction based on a result of the comparison by the comparison section.

27 Claims, 10 Drawing Sheets

Related U.S. Application Data

(60) Provisional application No. 61/861,654, filed on Aug. 2, 2013.

(52) U.S. Cl.
CPC ............... *A61B 2018/00642* (2013.01); *A61B 2018/00708* (2013.01); *A61B 2018/00791* (2013.01); *A61B 2018/00886* (2013.01); *A61B 2018/00994* (2013.01)

(58) Field of Classification Search
CPC ........... A61B 2018/00636; A61B 2018/00642; A61B 2018/00708; A61B 2018/00714; A61B 2018/00773; A61B 2018/00791; A61B 2018/00886; A61B 18/08; A61B 18/085; A61B 18/087; A61B 18/1442; A61B 18/1445
USPC ........... 606/2, 10–13, 27, 28, 31, 34, 40, 41; 607/88, 96, 100–102; 128/898
See application file for complete search history.

(56) References Cited

U.S. PATENT DOCUMENTS

| | | | |
|---|---|---|---|
| 2003/0069571 A1 | 4/2003 | Treat et al. | |
| 2003/0129382 A1 | 7/2003 | Treat | |
| 2003/0199864 A1 | 10/2003 | Eick | |
| 2005/0222556 A1* | 10/2005 | Ariura | A61B 18/20 606/12 |
| 2009/0076506 A1 | 3/2009 | Baker | |
| 2009/0157072 A1* | 6/2009 | Wham | A61B 18/1206 606/33 |
| 2009/0248002 A1 | 10/2009 | Takashino et al. | |
| 2013/0019060 A1 | 1/2013 | Wilkens et al. | |
| 2013/0338665 A1 | 12/2013 | Tanaka et al. | |
| 2014/0012155 A1 | 1/2014 | Flaherty et al. | |

FOREIGN PATENT DOCUMENTS

| | | |
|---|---|---|
| JP | 2005-253789 A | 9/2005 |
| JP | 2009-247893 A | 10/2009 |
| JP | 2014-508547 A | 4/2014 |
| WO | 98/38935 A1 | 9/1998 |
| WO | 01/12090 A1 | 2/2001 |
| WO | 2004/32596 A2 | 4/2004 |
| WO | 2012/071388 A2 | 5/2012 |
| WO | 2013/088892 A1 | 6/2013 |
| WO | 2013/094326 A1 | 6/2013 |
| WO | 2013/112238 A1 | 8/2013 |

OTHER PUBLICATIONS

Sep. 16, 2014 Search Report issued in International Patent Application No. PCT/JP2014/070348.

Mar. 21, 2017 Office Action issued in Japanese Patent Application No. 2015-228770.

* cited by examiner

LIVING TISSUE BONDING SYSTEM AND METHOD FOR OPERATING LIVING TISSUE BONDING SYSTEM

CROSS REFERENCE TO RELATED APPLICATION

This application is a continuation application of PCT/N2014/070348 filed on Aug. 1, 2014 and claims benefit of U.S. Provisional Patent Application No. 61/861,654 filed in the U.S.A. on Aug. 2, 2013, the entire contents of which are incorporated herein by this reference.

BACKGROUND OF THE INVENTION

1. Field of the Invention

Embodiments of the present invention relate to a living tissue bonding system provided with a sandwiching section applying treatment energy to a treated body and a method for operating the living tissue bonding system.

2. Description of the Related Art

A specification of U.S. Patent Application Publication No. 2009/076506 discloses a treatment system provided with: a pair of sandwiching sections applying high frequency power energy and heat energy to a treated body sandwiched by the pair of sandwiching sections; a high frequency power source outputting high frequency power for applying the high frequency power energy; a power source for heat generation outputting power for heat generation for applying the heat energy; a control section controlling the high frequency power source and the power source for heat generation for switching between application of the high frequency power energy and application of the heat energy.

Further, a specification of U.S. Patent Application Publication No. 2009/0248002 discloses a treatment system which applies high frequency power energy to a treated body, and applies heat energy after application of the high frequency power energy ends. The high frequency power energy acts to, by destroying a cell membrane of a treated body, releases intracellular components including high molecular compounds including protein and equalizes the intracellular components with extracellular components including collagen. Then, the treated body is joined by application of the heat energy.

A specification of U.S. Patent Application Publication No. 2013/19060 discloses a treatment system which applies ultrasound energy and high frequency power energy to a treated body.

A specification of U.S. Patent Application Publication No. 2005/222556 discloses a treatment system which applies light energy to a treated body using a laser.

That is, a treatment section of a medical treatment instrument applies at least any of heat energy, ultrasound energy, light energy and high frequency power energy to a treated body as treatment energy.

SUMMARY OF THE INVENTION

A living tissue bonding system of an embodiment has: a sandwiching section for sandwiching living tissue; a power source for supplying to the living tissue treatment energy for bonding the living tissue sandwiched by the sandwiching section; a temperature measuring section for measuring a temperature of the living tissue sandwiched by the sandwiching section; a calculation section calculating, from the temperature of the living tissue measured by the temperature measuring section and a time period of applying the treatment energy, a time integral value of the temperature of the living tissue; a comparison section comparing the time integral value of the temperature of the living tissue calculated by the calculation section with a predetermined setting value; and an instruction section giving an instruction based on a result of the comparison by the comparison section.

A method for operating a living tissue bonding system of another embodiment includes the steps of a power source supplying to the living tissue treatment energy for bonding living tissue sandwiched by a sandwiching section; a temperature measuring section measuring a temperature of the living tissue sandwiched by the sandwiching section; a calculation section calculating, from the temperature of the living tissue measured by the temperature measuring section and a time period of applying the treatment energy, a time integral value of the temperature of the living tissue; a comparison section comparing the time integral value calculated by the calculation section with a predetermined setting value; and an instruction section giving an instruction based on a result of the comparison by the comparison section.

DETAILED DESCRIPTION OF THE PREFERRED EMBODIMENTS

First Embodiment

<Configuration of Treatment System>

Figure 1:
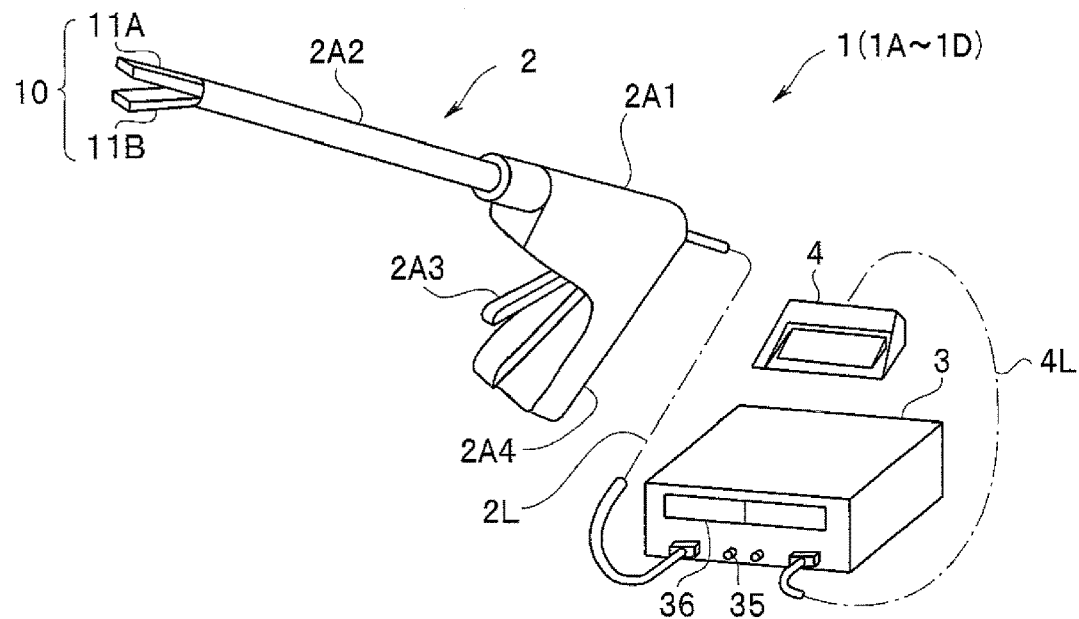
FIG. 1 is an external view of a treatment system of a first embodiment.

As shown in FIG. 1, a treatment system (living tissue bonding system) 1 of the present embodiment is provided with a treatment instrument 2, a body portion 3, which is a treatment instrument control apparatus, and a foot switch 4. The treatment instrument 2 is, for example, a surgical operation energy inosculation apparatus for performing joining treatment and the like of living tissue in an abdominal cavity through an abdominal wall.

The treatment instrument 2 has a grip 2A1, a shaft 2A2, and a treatment section 10 constituted by an openable pair of sandwiching sections 11 (a first sandwiching section 11A and a second sandwiching section 11B) for grasping living tissue LT, which is a treated body, to perform treatment.

Note that, hereinafter, at time of mentioning each of components having a same function and having reference numerals with A and B attached to ends of the reference numerals, respectively, the symbol A or B may be omitted. For example, each of the first sandwiching section 11A and the second sandwiching section 11B may be referred to as the sandwiching section 11.

The grip 2A1 is connected to the body portion 3 via a cable 2L. The grip 2A1 having an opening/closing knob 2A3 for a surgeon to operate opening and closing of the treatment section 10 is in such a shape that the surgeon can easily clasp, for example, in a substantially L shape. At one end of the grip 2A1, the grip 2A3 is arranged which is integrated with the treatment section 10 and which transmits operation of the opening/closing knob 2A3 to the treatment section 10. On the other hand, on the other end side of the grip 2A1, a grasping portion 2A4 to be grasped by the surgeon exists.

The body portion 3 has a display section 36 which displays treatment conditions and the like and a setting operation section 35 for the surgeon to set the treatment conditions and the like on a front panel, and the foot switch 4 is connected to the body portion 3 via a cable 4L. By the surgeon performing a pressing operation of a pedal of the foot switch 4, power output from the body portion 3 to the treatment instrument 2 is on/off controlled. The foot switch 4 is not an essential component. A switch or the like which the surgeon operates at hand is also possible.

Figure 2A:
FIG. 2A is a side view of a treatment section of the treatment system of the first embodiment.
Figure 2B:
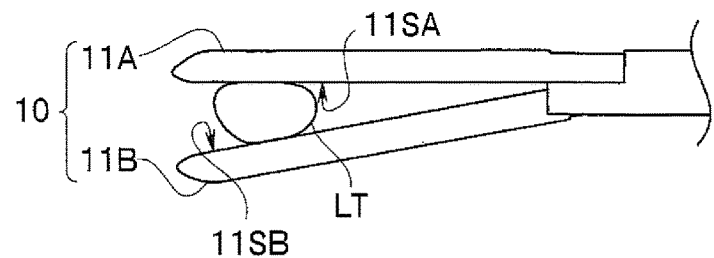
FIG. 2B is a side view of the treatment section of the treatment system of the first embodiment.

As shown in FIGS. 2A and 2B, the treatment instrument 2 applies heat energy (TH energy) to the living tissue LT via treatment surfaces 11SA and 11SB which are surfaces in contact with the living tissue LT.

The treatment section 10 can freely open and close, for example, by the second sandwiching section 11B moving relative to the first sandwiching section 11A. As shown in 2A, when a pressing operation of the opening/closing knob 2A3 is not performed by the surgeon, the second sandwiching section 11B is in a state of being close to or being in contact with the first sandwiching section 11A by urging force of an elastic member not shown. In comparison, as shown in FIG. 2B, when a pressing operation of the opening/closing knob 2A3 is performed by the surgeon with force stronger than the urging force of the elastic member, the second sandwiching section 11B is separated from the first sandwiching section 11A, and the treatment section 10 is in an open state. When the surgeon stops the pressing operation of the opening/closing knob 2A3, the living tissue LT inserted between the first sandwiching section 11A and the second sandwiching section 11B when the treatment section 10 is in the open state is kept in a state of being sandwiched and pressed between the treatment surface 11SA of the first sandwiching section 11A and the treatment surface 11SB of the second sandwiching section 11B by urging force of the elastic member.

Figure 3A:
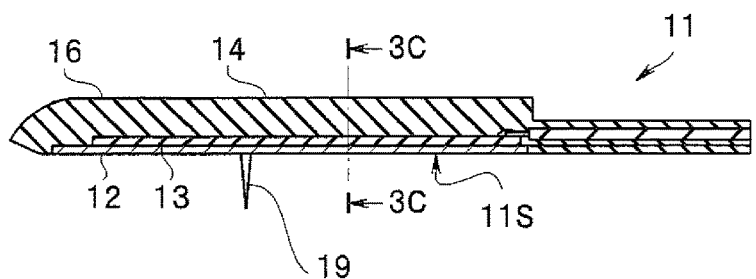
FIG. 3A is a cross-sectional view of the treatment section of the treatment system of the first embodiment.
Figure 3B:
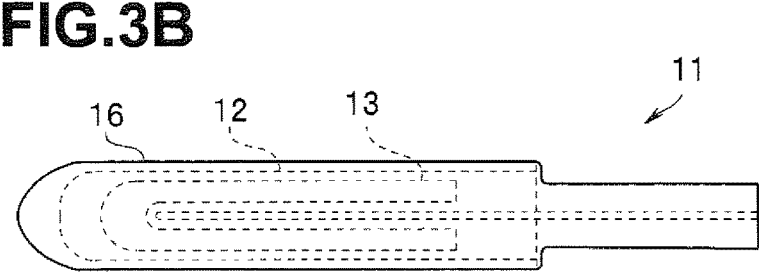
FIG. 3B is a top view of the treatment section of the treatment system of the first embodiment.
Figure 3C:
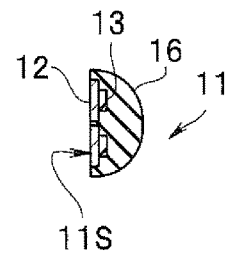
FIG. 3C is a cross-sectional view of the treatment section of the treatment system of the first embodiment along a 3C-3C line in FIG. 3A.
Figure 4:
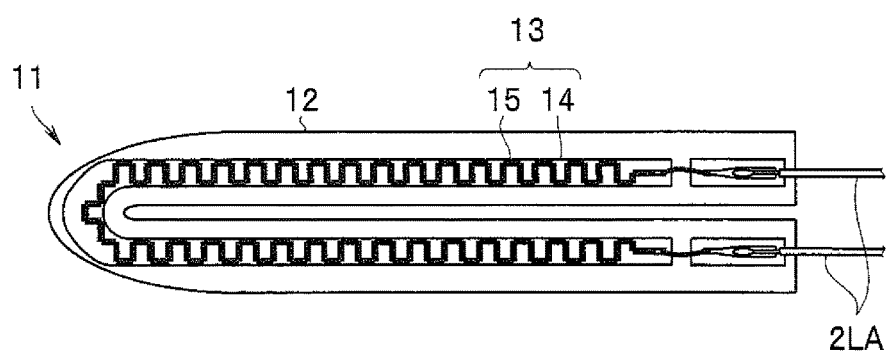
FIG. 4 is a top view of a heat generating section of the treatment system of the first embodiment.

As shown in FIGS. 3A to 4, the treatment surface 11S of the sandwiching section 11 is a front face (outer face) of a heat transfer body 12 made of metal such as stainless steel and copper. A heat generating device 13 is joined to a back face (inner face) of the heat transfer body 12. A top surface of the heat generating device 13 is covered by an insulator 16 such as polyimide and insulated.

In the heat generating device 13, a heat generation resistance body 15 is formed on a surface of a substrate 14 made of alumina, aluminum nitride or the like. The heat generation resistance body 15 is made of platinum with a positive temperature coefficient of resistance in which electrical resistance R increases as temperature increases. Therefore, a temperature T1 of the heat generating device 13 (the heat generation resistance body 15) can be calculated from the electrical resistance R of the heat generation resistance body 15. As material of the heat generation resistance body 15, various high melting point metal materials with a positive temperature coefficient of resistance, such as NiCr alloy, Ta and W, may be used.

The heat generating device 13 is an output section which applies power for heat generation (TH) outputted from the body portion 3 to the living tissue LT as heat energy.

Further, as shown in FIG. 3A, the treatment instrument 2 has a temperature sensor 19 which projects from the treatment surface 11S. For example, the temperature sensor 19 is included inside when the first sandwiching section 11A and the second sandwiching section 11B are closed. When the first sandwiching section 11A and the second sandwiching section 11B open, the temperature sensor 19 projects by the elastic body such as a spring. Then, the temperature sensor 19 is inserted into the living tissue LT sandwiched between the first sandwiching section 11A and the second sandwiching section 11B and detects a temperature (tissue temperature) T2 of the living tissue LT. Note that the tissue temperature T2 is lower relative to the temperature (device temperature) T1 of the heat generating device 13 by a temperature difference $\Delta T$.

$$T2 = T1 - \Delta T \qquad \text{(Equation 1)}$$

In a case of living tissue sandwiched between the treatment surface 11SA and the treatment surface 11SB, the tissue temperature T2 is, for example, a lowest temperature, that is, a temperature of living tissue at an intermediate portion between the treatment surface 11SA and the treatment surface 11SB. Instead of the internal temperature of the tissue, the tissue temperature T2 may be a surface temperature of a part in contact with the treatment surface 11S if the tissue temperature is a temperature of living tissue being treated.

The heat generating device 13 is arranged on each of the sandwiching sections 11A and 11B. The heat generating device 13, however, only has to be arranged on at least one of the sandwiching sections 11.

Next, a configuration of the treatment system 1 will be described with use of FIG. 5. As already described, the treatment system 1 has the treatment instrument 2, the body portion 3 and the foot switch 4.

The body portion 3 is provided with a power source 30 for power for heat generation (TH), a power-for-heat-generation sensor (TH sensor) 31, a setting section 32, a calculation section 33, a control section 34 and a temperature measuring section 39.

The power source 30 outputs power for heat generation (TH) for heat energy. The TH sensor 31, which is a detection section, detects an output value (voltage and current) of the TH. Power P is a product of the voltage and the current.

The control section 34 includes a comparison section 34A, an instruction section 34B and a power source control section 34C and performs control of the entire treatment system 1.

The temperature measuring section 39 measures the temperature (tissue temperature) T2 of living tissue to which heat energy is applied, from an output of the temperature sensor 19.

The calculation section 33 calculates the electrical resistance R of the heat generating device 13 from the voltage and current of the power TH and calculates the temperature (device temperature) T1 of the heat generating device from the calculated electrical resistance R. That is, the calculation section 33 has a storage section (not shown) in which a calculation formula based on a temperature coefficient of resistance of the heat generating device 13 or a table of correspondence between the electrical resistance R and the device temperature T1 or the like is stored. Note that the calculation section 33 may directly calculate the device temperature T1 from the voltage and current of the TH without calculating the electrical resistance R.

The calculation section 33 also calculates a heating amount Q which is a time integral value of the living tissue temperature T2. The heating amount Q is a product of temperature and an application time period and is shown, for example, in a unit of "° C. second". For example, a heating amount Q from start of treatment (time 0) to time t is calculated by (Equation 2) below.

$$Q = \int_0^t T2 \, dt \qquad \text{(Equation 2)}$$

The heating amount Q can be also expressed as an accumulated temperature in a unit of "° C." which is obtained by adding up the living tissue temperature T2 measured for each predetermined time period, for example, every one second. That is, the time integral value and the accumulated temperature are physical quantities showing a same state though the units are different. Note that the heating amount Q is a physical quantity which is quite different from an amount of heat (calories) indicated in a unit of joules.

The setting section 32 sets treatment conditions based on an operation and the like of the setting operation section 35. In the treatment system 1, the setting section 32 has a storage section 32M. The storage section 32M constituted by a semiconductor memory or the like may store a plurality of different treatment conditions such as a heating amount setting value Qset to be described later. Note that the setting operation section 35 can be regarded as a part of the setting section 32 in a broad sense.

A CPU or the like constituting the control section 34 may have at least a part of functions of the temperature measuring section 39, the calculation section 33 and the setting section 32. Each may be an independent CPU. Further, the storage section 32M of the setting section may have functions of the storage section of the calculation section 33.

The display section 36 is a notification section which notifies the surgeon of information such as set treatment conditions, an output value of power during treatment and the tissue temperature T2.

The comparison section 34A compares the time integral value (the heating amount Q) of the temperature of living tissue calculated by the calculation section 33 and a predetermined setting value (the heating amount setting value Qset). The instruction section 34B gives an instruction based on a result of the comparison by the comparison section 34A. The power source control section 34C controls the power source 30 so that application of treatment energy decreases or ends, based on the instruction from the instruction section 34B. Further, instead of the control by the power source control section 34C, a display to the effect that a treatment is to be ended may be shown on the display section 36 based on the instruction from the instruction section 34B, or a sound may be generated from a speaker as the notification section. Of course, it is also conceivable that the power source control section 34C controls the power source 30, and, further, the notification section makes a notification.

That is, in the treatment system 1, the comparison section 34A compares the heating amount Q calculated by the calculation section 33 and the heating amount setting value Qset which is a predetermined setting value set by the setting section 32. When the heating amount Q becomes the heating amount setting value Qset or above, the instruction section 34B gives an instruction to the power source control section 34C. The power source control section 34C controls the TH power source 30 so that application of treatment energy to the living tissue LT decreases or ends, based on the instruction.

<Method for Operating Treatment System>

Next, a method for operating the treatment system 1 will be described along a flowchart of FIG. 7.

<Step S11>

For example, treatment conditions including the heating amount setting value Qset as shown below are set via the setting section 32 including the setting operation section 35.

Device temperature setting value Tset: 220° C.
Heating amount setting value Qset: 800° C. second
Lower limit temperature Tmin: 50° C.
Upper limit temperature Tmax: 230° C.

Here, the device temperature setting value Tset is a target temperature of the heat generating device 13 to be constant-temperature controlled. Note that the device temperature setting value Tset may be a target temperature of the tissue temperature. The lower limit temperature Tmin is a temperature at which change begins to occur in living tissue. In other words, the living tissue is not treated substantially until the lower limit temperature Tmin is reached. The upper limit temperature Tmax is a temperature at which living tissue being treated is damaged beyond expectation, and a possibility that a surrounding site is adversely affected begins to occur.

As already described, though a treatment time period (a treatment energy application time period) is set as a treatment condition in a conventional treatment system, the heating amount setting value Qset, which is the time integral value of the tissue temperature T2 until end of application of heat energy, is set in the treatment system 1.

Note that, though the treatment conditions can be set, for example, from among the plurality of treatment conditions stored in the storage section 32M by the surgeon according to treatment, the setting section 32 may automatically set the treatment conditions according to a kind of living tissue LT as described later.

That is, each condition may be set individually, or a plurality of conditions may be selected as a set of treatment conditions set in advance. For example, a plurality of sets of treatment conditions LV1 to LV3 may be stored in the storage section 32M in advance according to a kind of living tissue LT to be treated, as described below.

(LV1)
Device temperature setting value Tset: 180° C.
Heating amount setting value Qset: 1000° C. second
Lower limit temperature Tmin: 50° C.
Upper limit temperature Tmax: 190° C.

(LV2)
Device temperature setting value Tset: 190° C.
Heating amount setting value Qset: 2500° C. second
Lower limit temperature Tmin: 50° C.
Upper limit temperature Tmax: 200° C.

(LV3)
Device temperature setting value Tset: 200° C.
Heating amount setting value Qset: 3500° C. second
Lower limit temperature Tmin: 50° C.
Upper limit temperature Tmax: 210° C.

<Step S12>

As shown in FIG. 2A, the treatment section 10 in a closed state is inserted, for example, into an abdominal cavity through an abdominal wall. When the surgeon performs a pressing operation of clasping the opening/closing knob 2A3 of the grip 2A1, the second sandwiching section 11B opens relative to the first sandwiching section 11A. Then, treatment target living tissue LT is arranged between the treatment surface 11SA of the first sandwiching section 11A and the treatment surface 11SB of the second sandwiching section 11B. When the opening/closing knob 2A3 is released in this state, the second sandwiching section 11B is closed relative to the first sandwiching section 11A by urging force of the elastic member, and the treatment target living tissue LT is sandwiched between the treatment surface 11SA of the first sandwiching section 11A and the treatment surface 11SB of the second sandwiching section 11B in a pressed state as shown in FIG. 2B.

<Step S13>

The surgeon performs a pressing operation of the foot switch 4 with a foot. Then, the control section 34 performs control so that the power source 30 outputs power for heat generation (TH). The control section 34 starts constant-temperature control of an output value P of the power source 30 so that the device temperature T1 becomes the device temperature setting value Tset.

In the treatment system 1, an average temperature of the heat generating devices 13A and 13B or a temperature of one of the heat generating devices 13A and 13B is regarded as the device temperature T1 to control one power source 30. However, the temperature of each of the heat generating devices 13A and 13B may be calculated to perform control with a power source for each of them.

<Step S14>

The temperature measuring section 39 measures the tissue temperature T2.

<Step S15>

The control section 34 judges whether the tissue temperature T2 has increased to the lower limit temperature Tmin or above. If the tissue temperature T2 has become the lower limit temperature Tmin or above (YES), the flow proceeds to step S16.

Therefore, the heating amount Q is not calculated during a period during which the tissue temperature T2 is below the lower limit temperature Tmin (a period from the time 0 to time t0).

<Step S16>

The control section 34 judges whether the tissue temperature T2 has increased to the upper limit temperature Tmax or above. If the tissue temperature T2 becomes the upper temperature Tmax or above (YES), the flow proceeds to step S19 to stop the treatment. It is desirable that, at this time, the control section 34 displays a warning on the display section 36.

Note that the control based on the lower limit temperature Tmin and the upper limit temperature Tmax is not essential control of the treatment system 1 of the embodiment.

<Step S17>

The calculation section 33 calculates the heating amount Q which is the time integral value of the tissue temperature T2. The heating amount Q shown by (Equation 2) is obtained by adding ΔQ (tissue temperature T2×1 second) to heating amount Q accumulated so far, for example, every one second.

<Steps S18 and S19>

The comparison section 34A of the control section 34 compares the heating amount Q and the heating amount setting value Qset. When the heating amount Q becomes the heating amount setting value Qset or above (YES), an instruction signal is outputted from the instruction section 34B to the power source 30, and the power source control section 34C controls the power source 30 to end the output of the TH. That is, the output of the TH ends based on the heating amount setting value Qset and the heating amount Q.

That is, step S18 is constituted by step S18A of the comparison section 34A comparing the time integral value (the heating amount Q) calculated by the calculation section 33 with a predetermined setting value (the heating amount setting value Qset), step S18B of the instruction section 34B giving an instruction based on a result of the comparison by the comparison section 34A and step S18C of the power source control section 34C controlling the power source 30 based on the instruction from the instruction section 34B.

Note that the power source control section 34C may control the power source 30 to decrease the output of the TH to a level at which the output of the TH substantially does not influence living tissue.

Figure 8:
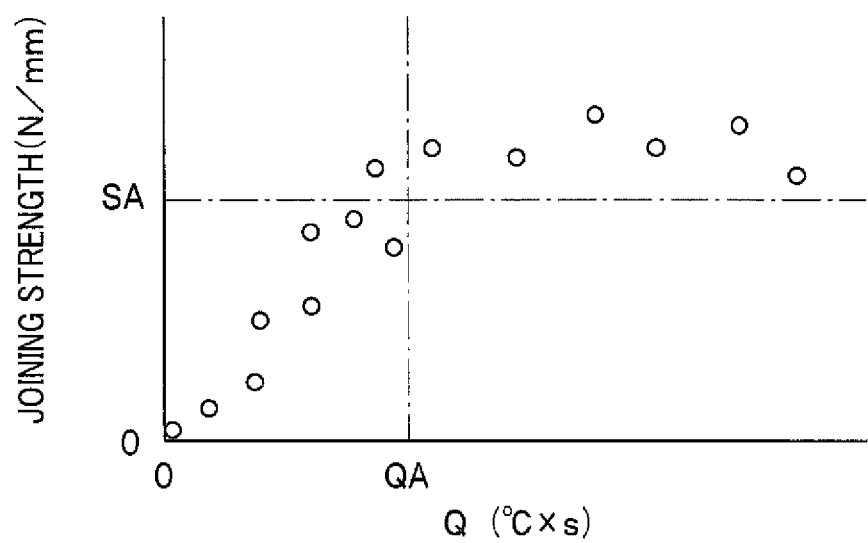
FIG. 8 is a graph showing a relationship between the heating amount and joining strength of the living tissue in the treatment system of the first embodiment.

FIG. 8 shows a relationship between the heating amount Q and joining strength of treated living tissue LT. It is apparent from FIG. 8 that a good treatment result can be obtained by being based on the heating amount Q. That is, if the heating amount Q is a predetermined heating amount QA or larger, practically sufficient joining strength SA can be obtained. The heating amount setting value Qset determined based on experimental values of the heating amount QA is stored in the storage section 32M.

Note that, by performing similar control based on a heating amount calculated from a time integral value of the device temperature T1, a better treatment result can be obtained also in comparison with the conventional control which is based on a time period. In order to perform more appropriate treatment, however, it is preferable to perform control based on a heating amount calculated from the time integral value of the tissue temperature T2.

Further, it is also conceivable that, as a target temperature of constant-temperature control, a tissue temperature setting value is set instead of the device temperature setting value Tset, and the control section 34 controls the output value P of TH power so that the tissue temperature T2 becomes the tissue temperature setting value.

As described above, the body portion 3, which is a treatment instrument control apparatus has: a treatment instrument applying treatment energy to living tissue; a power source outputting power to be converted to the treatment energy; a temperature measuring section for measuring a temperature of the living tissue; a calculation section calculating, from the temperature measured by the temperature measuring section and a time period of applying the treatment energy, a time integral value of the temperature; a comparison section comparing the time integral value of the temperature calculated by the calculation section with a predetermined setting value; and an instruction section giving an instruction based on a result of the comparison by the comparison section.

Further, a method for operating the treatment system includes the steps of: a power source outputting power; a treatment instrument converting the power to treatment energy and treating living tissue; a temperature measuring section measuring a temperature of the living tissue to which the treatment energy is applied; a calculation section calculating, from the measured temperature of the living tissue and a time period of applying the treatment energy, a time integral value of the temperature of the living tissue; a comparison section comparing the time integral value calculated by the calculation section with a predetermined setting value; and an instruction section giving an instruction based on a result of the comparison by the comparison section.

Because a heat energy application time period is controlled based on the heating amount Q in the treatment system 1, a good treatment result can be easily obtained. That is, the treatment system 1, the body portion 3 which is a treatment instrument control apparatus, and the method for operating the treatment system 1 have a good operability.

Note that the temperature measuring section 39 may estimate the tissue temperature T2 from the device temperature T1 and the output value P of power (TH). That is, the temperature measuring section 39 may indirectly measure the tissue temperature T2 via the output value P and the like without directly measuring it by a temperature sensor or the like.

Figure 9:
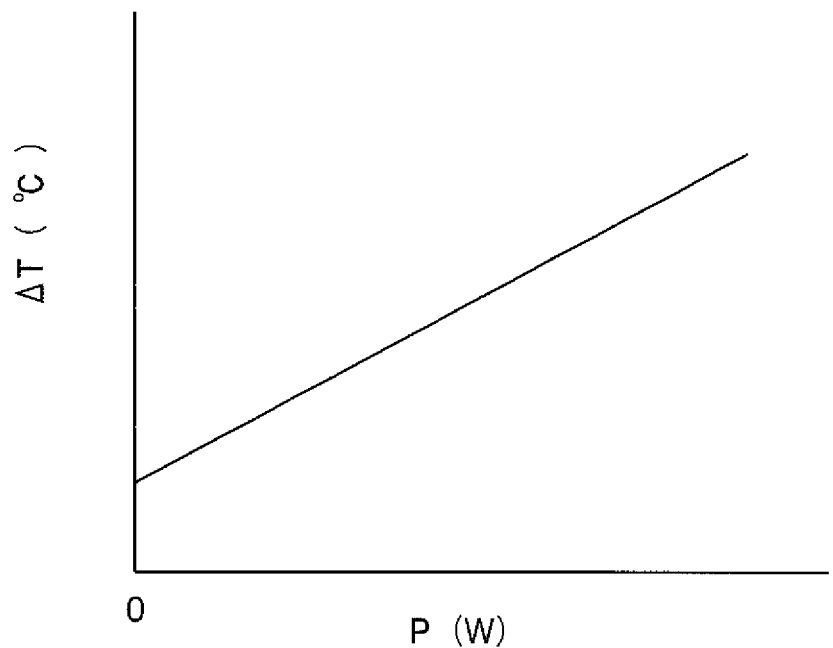
FIG. 9 is a graph showing a relationship between temperature difference between tissue temperature and treatment section temperature, and an output value of power for heat generation in a treatment system of a modification 1 of the first embodiment.

The output value P is constant-temperature controlled so that the device temperature T1 becomes the predetermined device temperature setting value Tset. Therefore, when the temperature difference ΔT is large, TH with a larger output value P is required. That is, as shown in FIG. 9, the temperature difference ΔT is strongly correlated with the output value P of the power for heat generation (TH). Note that the temperature difference ΔT in FIG. 9 is based on experimental values obtained by actually measuring the tissue temperature T2 with a temperature sensor similar to the temperature sensor 19.

Therefore, T2 can be calculated from (Equation 3) below.

$$T2=T1-\Delta T=T1-f(P) \quad \text{(Equation 3)}$$

In the treatment system in which the temperature measuring section 39 calculates the temperature T1 of the heat generating device 13 from electrical resistance of the heat generating device 13 and further estimates the temperature T2 of living tissue from the temperature T1 of the heat generating device 13 and the output value P of power, a temperature sensor is unnecessary, and the calculation section 33 may have the functions of the temperature measuring section 39. Note that f(P) is acquired by experiments in advance and stored in a storage section (not shown) as an equation or a table (table data). A straight line shown in FIG. 9 indicates an example of performing linear expression approximation of a plurality of pieces of experimental data (plots) by a least squares method.

That is, f(P), an expression of the straight line shown in FIG. 9, is $\Delta T=\alpha P+\beta$ (α: slope; β: y-intercept). The expression f(P) may be a quadratic expression or the like or may be constituted by a plurality of different expressions for sections obtained by separating the power P into a plurality of ranges. In a case of storing f(P) as a table, corresponding ΔT is stored in the table, for example, for every 5 W of the power P.

Figure 10:
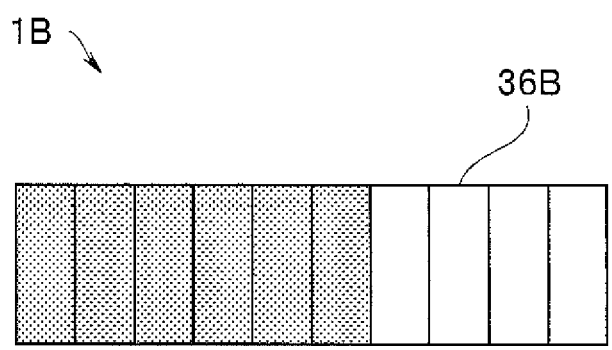
FIG. 10 is a diagram showing a display form of a display section which is a notification section in a treatment system of a modification 2 of the first embodiment.

Further, it is favorable that Q/Qset, a ratio of the heating amount Q calculated by the calculation section 33 to the heating amount setting value Qset, is displayed on a notification section 36B of the display section 36. For example, as shown in FIG. 10, the instruction section 34B gives an instruction to the notification section 36B based on a result of comparison by the comparison section 34A. Then, a state of progress of treatment is displayed like a bar graph on the notification section 36B. The surgeon can confirm the state of progress of treatment by the display on the notification section 36B.

Note that notification to the surgeon by a notification section is not limited to the notification section 36B of the display section 36 if the surgeon can recognize the notification. A notification section which makes the notification by a sound (voice information, kinds of melodies, change in frequency), vibration strength or the like is also possible.

Modifications of First Embodiment

Next, treatment systems 1A to 1C, treatment instrument control apparatuses and methods for operating the treatment systems of modifications 1 to 3 of the first embodiment will be described. Note that, hereinafter, (the treatment system, the treatment instrument control apparatus, and the method for operating the treatment system 1) will be referred to as the treatment system and the like. Since the treatment systems 1A to 1C and the like are similar to the treatment system 1 and the like, components having same functions are given same reference numerals, and description of the components will be omitted.

In the treatment system 1, applied treatment energy is heat energy. However, similar advantageous effects can be obtained if the treatment energy is any of heat energy, ultrasound energy, light energy and high frequency power energy.

<Modification 1>

In the treatment system 1A and the like of the modification 1, a laser beam, which is light energy, is applied to living tissue as treatment energy. That is, a power source outputs power to a light source which generates the laser beam.

The living tissue to which the laser beam is applied generates heat. It is also possible to selectively heat a particular treatment site by selecting a wavelength of the laser beam. The temperature measuring section 39 measures the tissue temperature T2 based on a detection result of an infrared thermometer.

<Modification 2>

In the treatment system 1B and the like of the modification 2, ultrasound energy is applied to living tissue as treatment energy. That is, a power source outputs power to an ultrasound transducer.

A treatment instrument of the treatment system 1C has the ultrasound transducer inside the grip 2A1, and the sandwiching section 11A ultrasonically vibrates back and forth. The living tissue sandwiched between the sandwiching section 11A which vibrates and the sandwiching section 11B which does not vibrate generates heat by frictional heat. In the treatment system 1C, the tissue temperature T2 is detected, for example, by a temperature sensor which detects a temperature of the treatment surface 11SB of the sandwiching section 11B.

<Modification 3>

In the treatment system 1C and the like of the modification 3, high frequency power energy is applied to living tissue as treatment energy. That is, a power source outputs high frequency power.

The heat transfer body of a treatment instrument of the treatment system 1C, which is made of metal, has a function as electrodes which apply high frequency power (HF) to the living tissue. When high frequency power is applied to living tissue LT sandwiched by electrodes 12A and 12B, the living tissue LT is heated by Joule heat.

All of the treatment systems 1A to 1C and the like of the modifications of the first embodiment have a good operability because an energy application time period is controlled based on the heating amount Q based on the temperature of living tissue similarly to the treatment system 1 and the like.

Second Embodiment

Next, a treatment system 1D and the like of a second embodiment will be described. Since the treatment system 1D and the like are similar to the treatment system 1 and the like, components having same functions are given same reference numerals, and description of the components will be omitted.

A treatment instrument 2D of the treatment system 1D applies high frequency power energy (HF energy) and heat energy (TH energy) to living tissue LT in turn via the treatment surfaces 11SA and 11SB.

The HF energy acts to, by destroying a cell membrane of living tissue, releases intracellular components including high molecular compounds including protein and equalizes the intracellular components with extracellular components including collagen. Further, the HF energy also acts to increase the temperature of the living tissue. Then, dehydration treatment and joining of the living tissue by application of heat energy, which are to be subsequently performed, are facilitated by the equalization and temperature increase of the living tissue.

Figure 11:
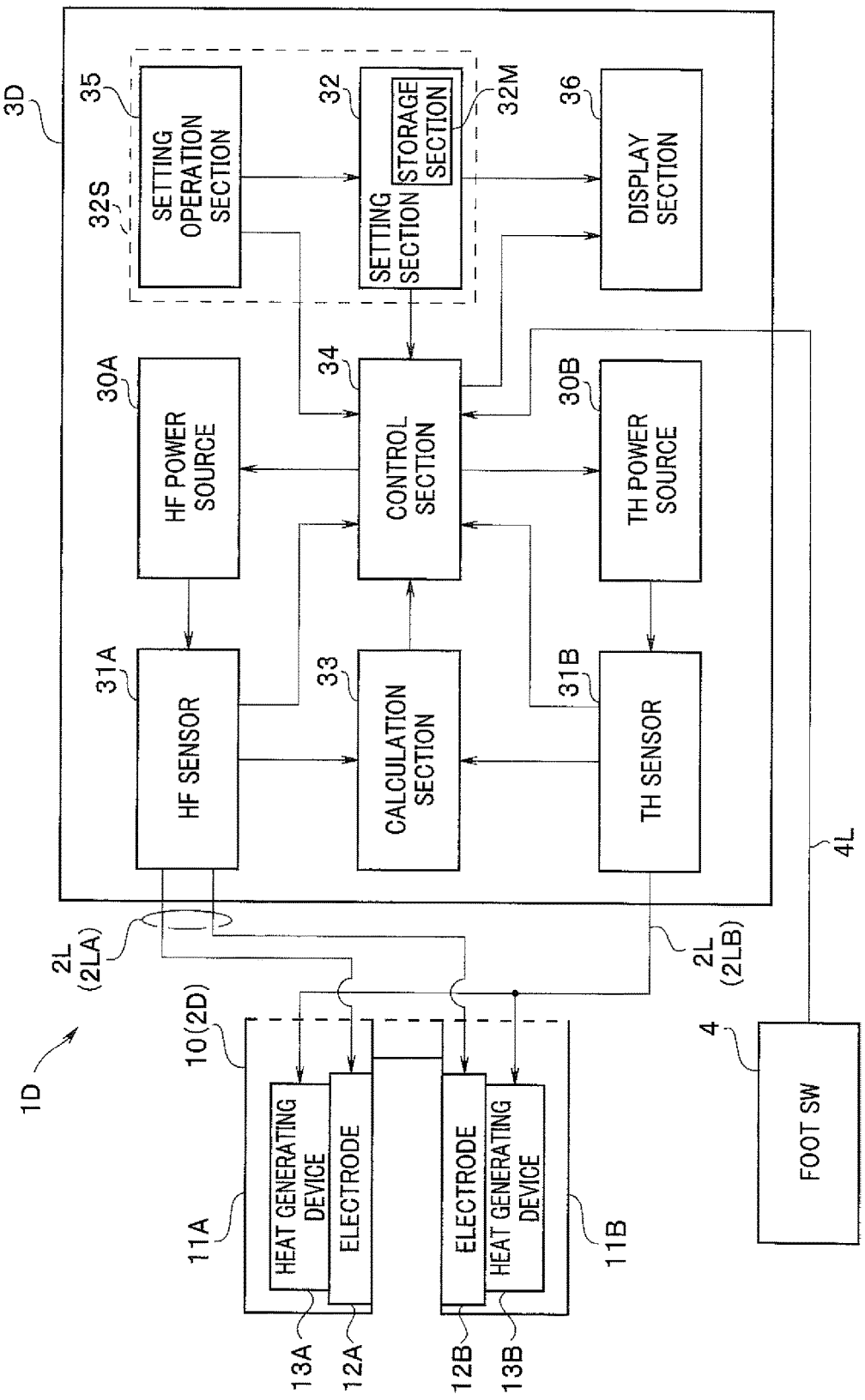
FIG. 11 is a configuration diagram of a treatment system of a second embodiment.

As shown in FIG. 11, the heat transfer body of the treatment instrument 2D of the treatment system 1D, which is made of metal, also has functions as the electrodes 12. A body portion 3D is provided with a power source 30A for high frequency power (HF) which is a first power source, a power source 30B for power for heat generation (TH) which is a second power source, an HF sensor 31A, a TH sensor 31B, the setting section 32, the calculation section 33 and the control section 34. Note that, in the treatment system 1D, the temperature T2 of living tissue is estimated from the temperature T1 of the heat generating device 13 and the output value P of power, and the calculation section 33 has the functions of the temperature measuring section 39.

Figure 5:
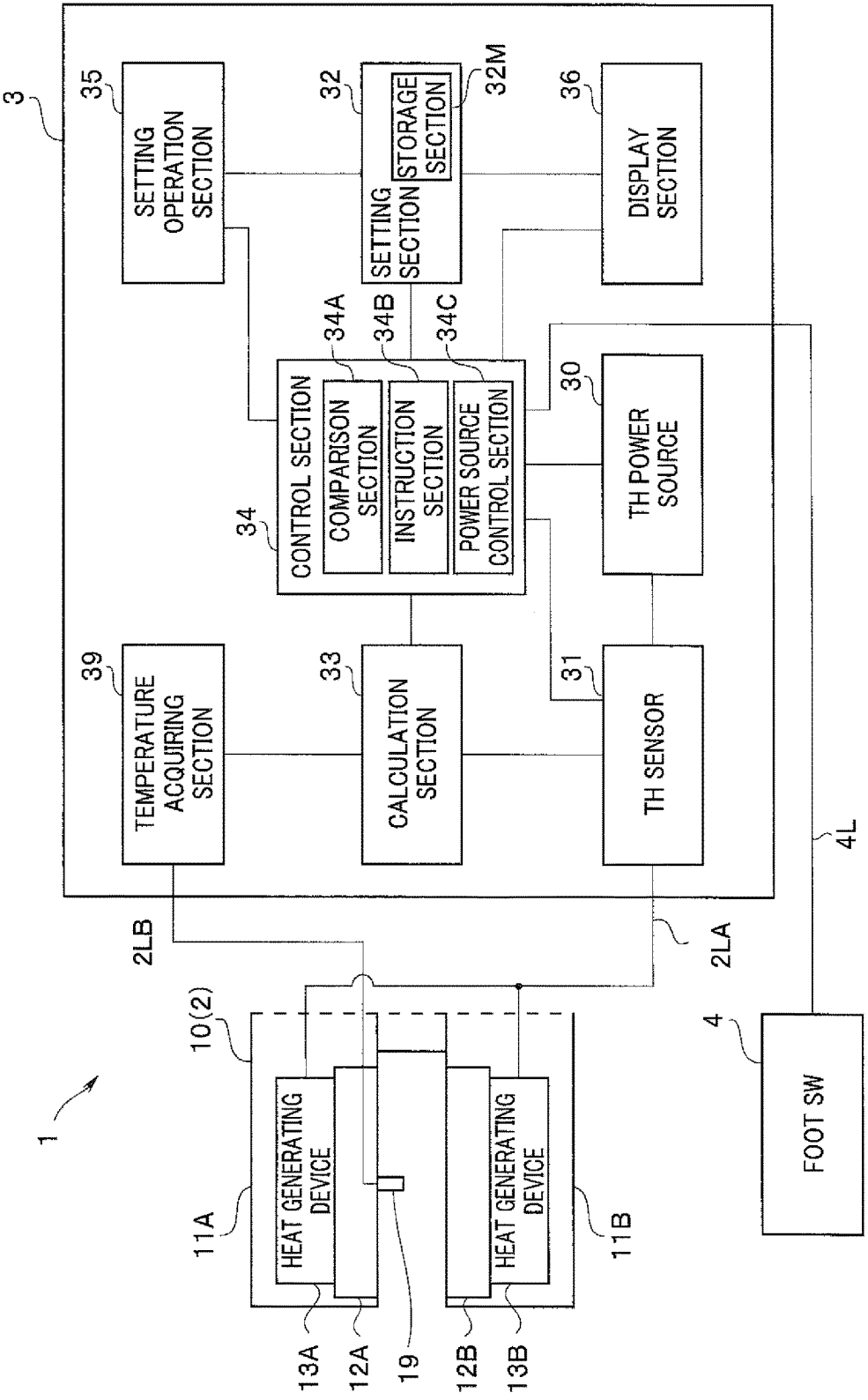
FIG. 5 is a configuration diagram of the treatment system of the first embodiment.
Figure 6:
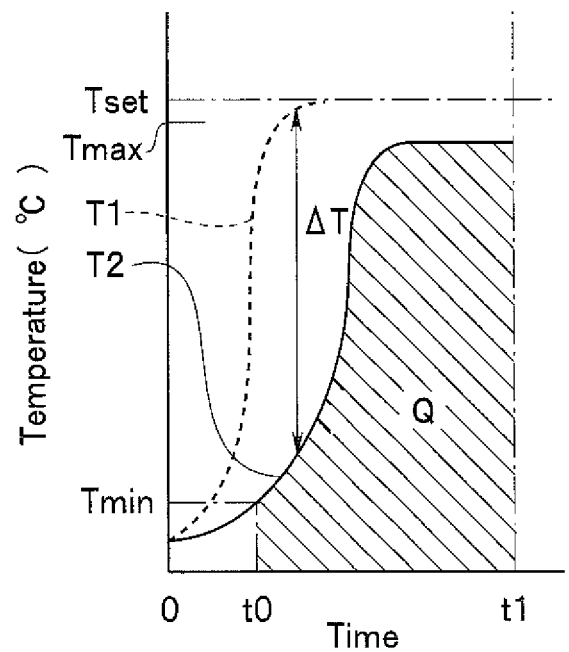
FIG. 6 is a graph for illustrating changes in temperatures of living tissue and the treatment section and a heating amount in the treatment system of the first embodiment.

Note that the control section 34 includes the comparison section 34A, the instruction section 34B and the power source control section 34C similarly as in FIG. 5 though it is not shown in FIG. 11.

The HF power source 30A outputs high frequency power (HF) which is first power. The TH power source 30B outputs power for heat generation (TH) which is second power. Note that, since the HF power source 30A and the TH power source 30B do not output power at the same time, one common power source may be used. In this case, a common sensor may be used as the HE sensor 31A and the TH sensor 31B.

The HF sensor 31A, which is a first detection section, detects an output value (voltage and current) of HF. The TH sensor 31B, which is a second detection section, detects an output value (voltage and current) of TH.

<Method for Operating Treatment System>

Figure 12:
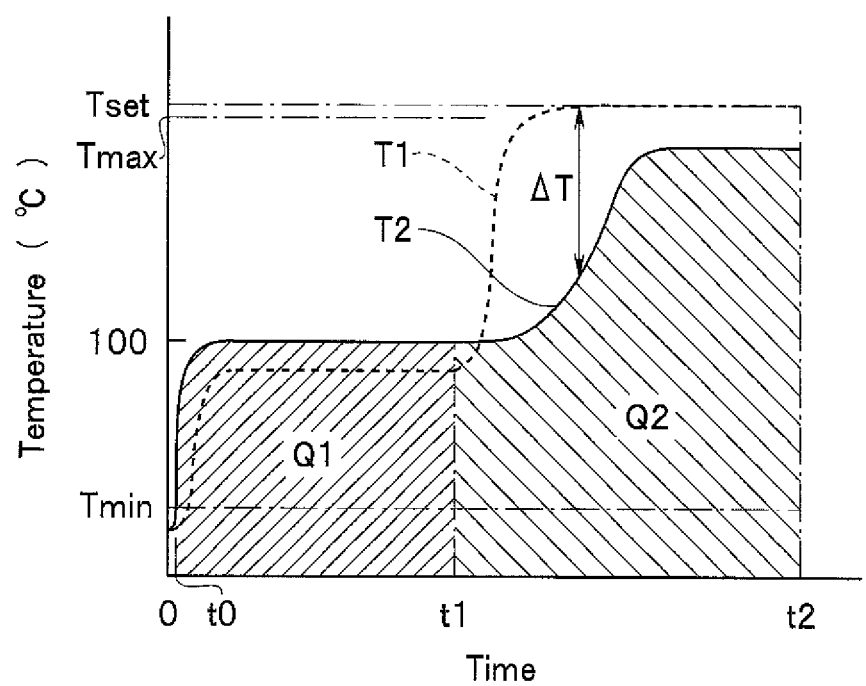
FIG. 12 is a flowchart for illustrating a method for operating the treatment system of the second embodiment.

As shown in FIG. 12, in the treatment system 1D, application of TH energy is started (time t=t1) after application of HF energy ends. Then, the control section 34 controls end of treatment (time t=t2) based on the time integral value of the tissue temperature T2 defined by the heating amount Q.

That is, when a total heating amount QT, which is a sum total of a heating amount of high frequency power energy (a first heating amount) Q1 by the application of the HF energy and a heating amount of heat energy (a second heating amount) Q2 by the application of the TH energy becomes the heating amount setting value Qset set in advance or above (time t=t2), the control section 34 performs control so that the TH power source 30B ends the application of the TH energy. That is, the following expression is satisfied:

$$Qset \leq Q1+Q2 \quad \text{(Expression 4)}$$

$$Q1 = \int_{t0}^{t1} T2 \, dt$$

$$Q2 = \int_{t1}^{t2} T2 \, dt$$

Figure 13:
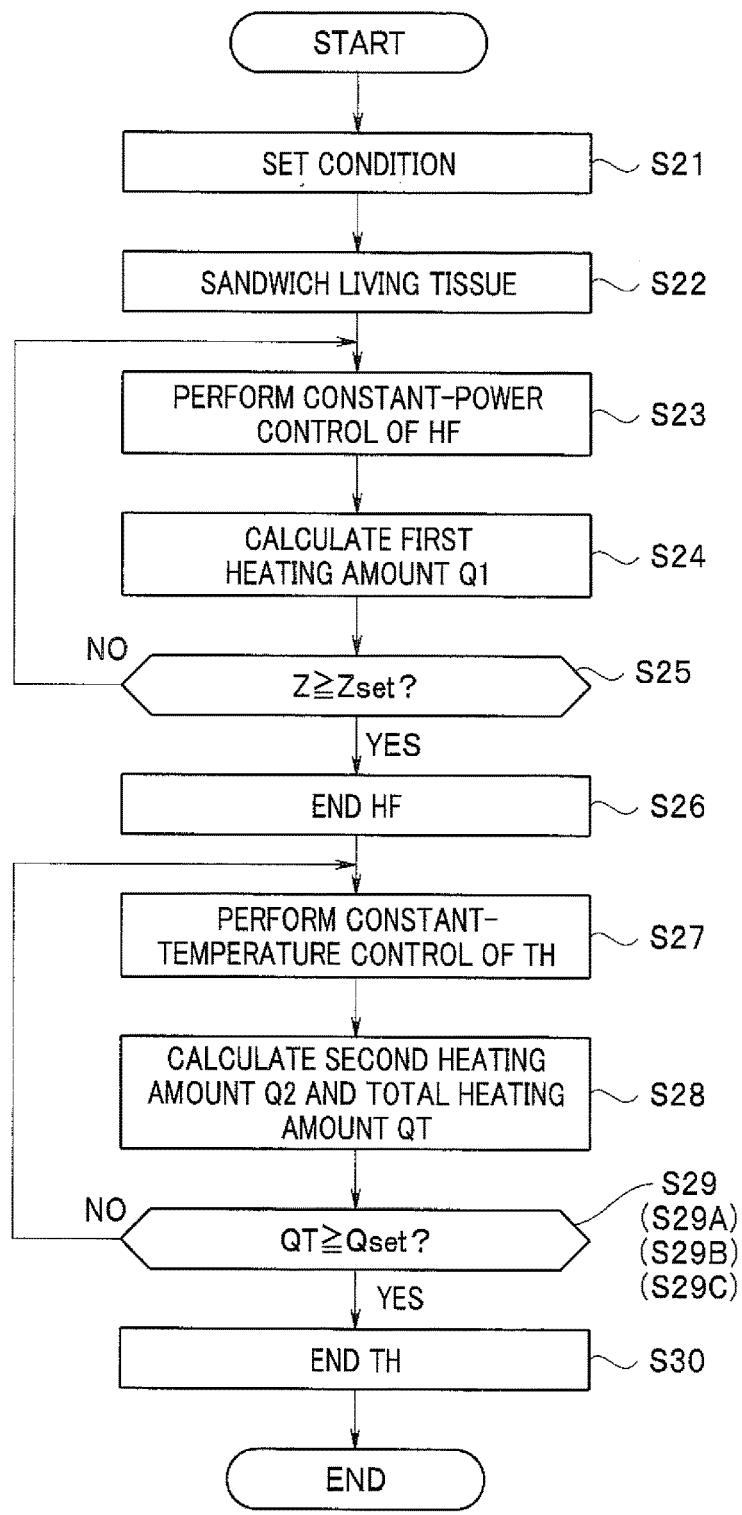
FIG. 13 is a graph for illustrating changes in temperatures of living tissue and a treatment section and a heating amount in the treatment system of the second embodiment.

Next, a method for operating the treatment system 1D will be described in detail along a flowchart of FIG. 13.

<Step S21>

For example, treatment conditions as shown below are set by the setting section 32 including the setting operation section 35.

HF output setting value Pset: 60 W
HF end impedance Zset: 120 Ω
Device temperature setting value Tset: 180° C.
Heating amount setting value Qset: 1000° C. second Note that the device temperature setting value Tset is set to a temperature exceeding 70° C. higher than the tissue temperature (100° C.±30° C.) at time when the application of HF ends, for example, a temperature exceeding 100° C.

Further, similarly to the treatment system 1, a lower limit temperature Tmin and an upper limit temperature Tmax are also set, and the control section 34 performs control based on the lower limit temperature Tmin and the upper limit temperature Tmax. However, since the control is same as in the treatment system 1, description of the control will be omitted.

Note that the setting section 32 may automatically set the heating amount setting value Qset according to characteristics of living tissue LT sandwiched by the pair of sandwiching sections 11.

For example, the heating amount setting value Qset is automatically set based on at least one of an interval G between the pair of the sandwiching sections 11A and 11B between which the living tissue LT is sandwiched, and initial impedance of HF.

The interval G is information about a size of the living tissue LT which is a treated body. The initial impedance of HF is tissue information including an amount of moisture of the living tissue LT. Further, as the initial impedance of HF, a minimum impedance value, a time period during which the impedance is a predetermined value or below, and the like can be used.

Furthermore, when the surgeon selects an operation procedure by the setting operation section 35, treatment conditions for a series of treatments are set by the setting section 32. For example, when Treatment A ends, the setting section 32 may automatically set treatment conditions for Treatment B. For example, in a case where the operation procedure is "lung lobectomy", and (Treatment A) lobe artery sealing, (Treatment B) lung vein sealing, (Treatment C) lobar bronchus sealing and (Treatment D) sealing of substantial organs between lobes are to be continuously performed in turn, treatment conditions for the series of (Treatment A) to (Treatment D) are set only by the surgeon selecting the operation procedure. Therefore, a good operability is provided.

<Step S22>

The treatment target living tissue LT is sandwiched between the treatment surface 11SA of the first sandwiching section 11A and the treatment surface 11SB of the second sandwiching section 11B in a pressed state.

<Step S23>

The surgeon performs a pressing operation of the foot switch 4 by a foot in the state of the living tissue LT being sandwiched at the treatment section 10. Then, the control section 34 starts treatment. That is, the control section 34 first performs control so that the HF power source 30A outputs high frequency power (HF). The HF is transmitted to the electrodes 12A and 12B of the treatment instrument 2 via the cable 2L. Then, the high frequency power is applied to the living tissue LT sandwiched between the electrodes 12A and 12B, and the living tissue LT is heated by Joule heat.

That is, HF energy causes the living tissue itself existing on an energizing path of HF between the electrodes 12A and 12B to generate heat. Therefore, in the process of applying the HF energy, the tissue temperature T2 increases even at a central part of the living tissue LT without causing temperature unevenness even if the living tissue LT is thick. Note that, though the treatment section 10 does not generate heat, the device temperature T1 also increases due to heat transmission from the heated living tissue LT.

The control section 34 performs constant-power control of an output value P1 of the HF with the HF output setting value Pset, for example, 60 W based on the current and voltage of the HF detected by the HF sensor 31A.

<Step S24>

The calculation section 33 calculates a heating amount of high frequency power (a first heating amount) Q1 which is the time integral value of the tissue temperature T2.

The tissue temperature T2 may be measured by the temperature sensor 19 inserted into the living tissue LT, an infrared sensor or the like.

However, as shown in FIG. 12, the tissue temperature T2 at the time of applying the HF energy can be considered to be constant after drastically increasing at first because the living tissue LT includes water. That is, for example, at atmospheric pressure, even if the energy is applied, the temperature of the living tissue LT which includes water is kept at a temperature near a boiling point (100° C.) which is a constant temperature, for example, at 100° C.±30° C.

Therefore, the first heating amount Q1 after start of the treatment until time t may be calculated by (Expression 5) below without using a sensor or the like.

$$Q1 \approx T2 \times t \approx 100° \text{ C.} \times t \quad \text{(Expression 5)}$$

Furthermore, the calculation of the first heating amount Q1 by the calculation section 33 (step S24) may be performed with use of (Equation 6) below after step S26 to be described later.

$$Q1 = 100° \text{ C.} \times t1 \quad \text{(Equation 6)}$$

wherein t1 indicates an HF energy application time period.

<Step S25>

In the treatment system 1D, when application of the HF energy is started, impedance Z is calculated by the calculation section 33 from the voltage and current of the HF detected by the HF sensor 31A.

The impedance Z increases due to dehydration and the like accompanying degeneration of the living tissue LT accompanying progress of the treatment. The control section 34 performs the treatment from S23 until the impedance Z becomes the set HF end impedance Zset or above (NO).

<Step S26>

When the impedance Z becomes the set HF end impedance Zset or above (YES), the control section 34 controls the HF power source 30A to end the output of the HF at S26 (t=t1).

That is, the output of the HF ends based on the impedance Z of the HF.

<Step S27>

The control section 34 starts control to apply TH energy to the living tissue LT instead of the HF energy.

In application of the TH energy, the control section 34 performs constant-temperature control of an output value P2 of the TH power source 30B based on the device temperature T1 of the treatment section 10. In other words, the heat generating device 13 is controlled so that the device temperature setting value Tset set at S21 is obtained. Whether the TH is direct-current or high frequency power does not matter, and a frequency in the case of being high frequency power may be same as that of the HF.

Though the high frequency power (HF) applied from the electrode 12 to the living tissue LT heats the living tissue LT as Joule heat, the power for heat generation (TH) directly transmits heat energy to the living tissue LT. The heat (TH) energy transmitted to the living tissue LT via the treatment surfaces 11S can heat the living tissue LT until the tissue temperature T2 increases up to a temperature exceeding 100° C. according to the device temperature setting value Tset irrespective of a degenerated state of the living tissue LT, for example, an amount of moisture.

<Step S28>

The calculation section 33 calculates a second heating amount (a heat energy heating amount) Q2 which is the time integral value of the tissue temperature T2. That is, at S28, while the TH is being constant-temperature controlled based on the device temperature T1 calculated from the electrical resistance R, and heat energy is being applied to the living tissue LT, the second heating amount Q2, which is the time integral value of the tissue temperature T2, is calculated. Furthermore, the calculation section 33 calculates the total heating amount QT obtained by adding up the first heating amount Q1 and the second heating amount Q2.

<Steps S29 and S30>

When the total heating amount QT becomes the heating amount setting value Qset or above (YES), the control section 34 controls the TH power source 30B to end output of the TH (t=t2). That is, the output of the TH ends based on the heating amount setting value Qset and the total heating amount QT.

Figure 7:
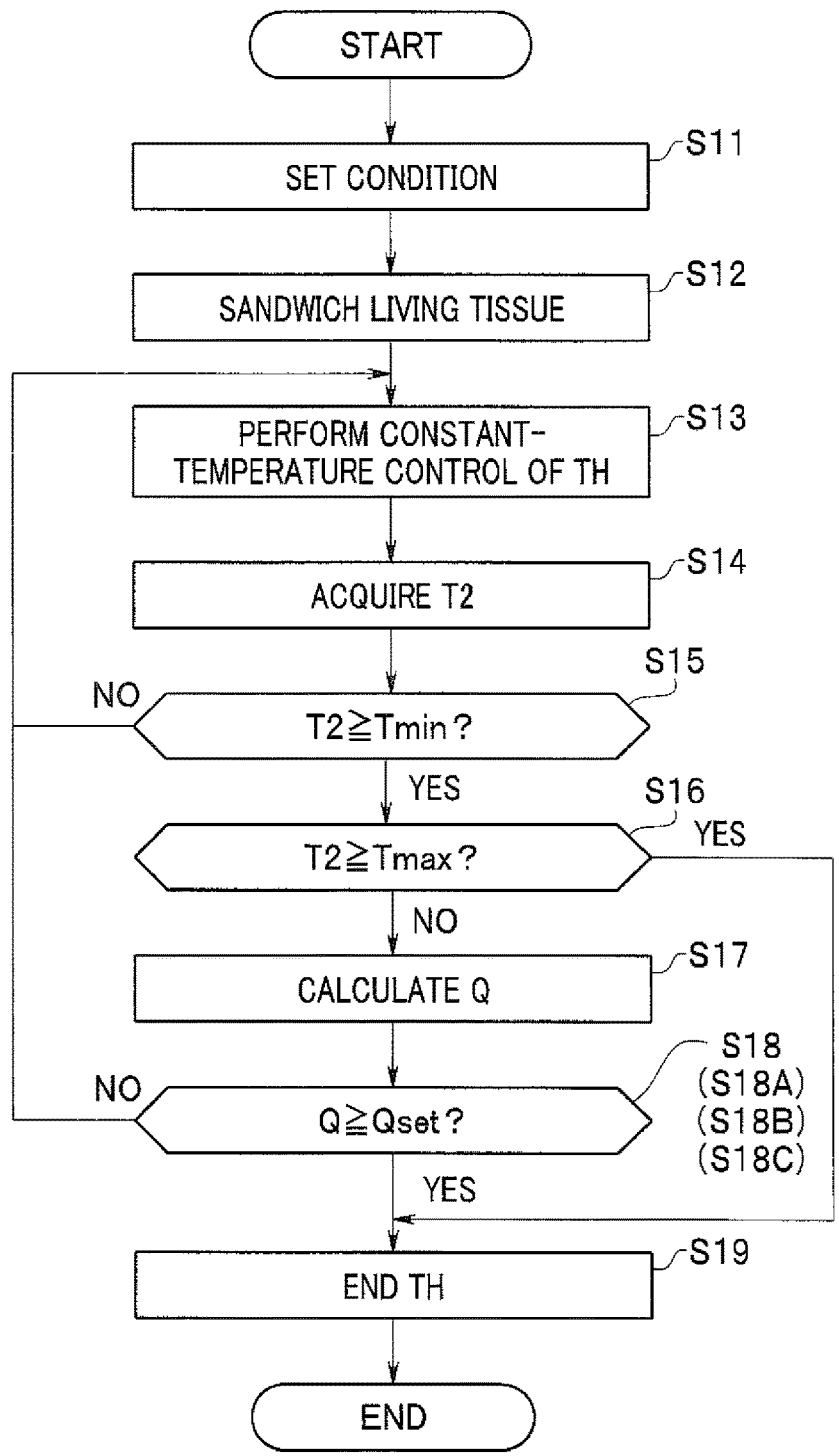
FIG. 7 is a flowchart for illustrating a method for operating the treatment system of the first embodiment.

Note that, similarly to step S18 shown in FIG. 7, step S29 is constituted by step S29A of the comparison section 34A comparing the time integral value (the total heating amount QT) calculated by the calculation section 33 with a predetermined setting value (the heating amount setting value Qset), step S29B of the instruction section 34B giving an instruction based on a result of the comparison by the comparison section 34A and step S29C of the power source control section 34C controlling the power source 30 based on the instruction from the instruction section 34B.

Here, since the first heating amount Q1 is already calculated and does not increase or decrease in the process at and after S26, the control section 34 may end the output of the TH when a remaining heating amount ΔQ shown by (Equation 7) below becomes zero.

Remaining heating amount ΔQ=Heating amount setting value Qset−First heating amount Q1−Second heating amount Q2 (Equation 7)

Note that the total heating amount QT or the remaining heating amount ΔQ may be calculated by the control section 34. Furthermore, only control by the second heating amount Q2 may be performed without calculating the first heating amount Q1. That is, only decreasing or ending of the heat energy may be performed based on the heating amount Q.

Since an energy application time period, that is, end of application of energy is controlled with use of the heating amount Q of the living tissue temperature T2 in the treatment system 1D, a good treatment result can be easily obtained. Therefore, the treatment system 1D, the body portion 3D which is a treatment instrument control apparatus, and the method for operating the treatment system 1D have a good operability.

Note that description has been made above on a case where first energy applied first is high frequency power energy, and second energy applied next is heat energy. However, similar advantageous effects can be obtained if the first energy is any of high frequency power energy, heat energy, light energy and ultrasound energy, and the second energy is any energy different from the first energy.

That is, a treatment system in which a treatment instrument applies two or more treatment energies selected from among heat energy, ultrasound energy, light energy and high frequency power energy to living tissue in turn, and a control section decreases or ends output of at least any treatment energy based on a heating amount has advantageous effects similar to those of the treatment system 1D.

For example, in a case of a treatment system in which a blood vessel is cut off by application of ultrasound energy after bleeding of the blood vessel is stopped by application of HF energy, similar advantageous effects can be obtained by performing control similar to that of the treatment system 1D.

Further, though description has been made on a bipolar treatment instrument in which living tissue LT is grasped by the pair of sandwiching sections 11, a good treatment result can be easily obtained even by a mono-polar treatment instrument if the treatment system is similarly controlled based on the total heating amount QT.

The present invention is not limited to the embodiments and the like described above, and various changes, alterations and the like can be made within a range not changing the spirit of the present invention.

What is claimed is:

1. A living tissue bonding system comprising:
a sandwiching section for sandwiching living tissue;
a power source for supplying treatment energy to the living tissue for bonding the living tissue sandwiched by the sandwiching section;
a temperature measuring section for measuring a temperature of the living tissue sandwiched by the sandwiching section; and
a processor and a memory, the processor being programmed to:
calculate, from the measured temperature of the living tissue and a time period of applying the treatment energy, a time integral value of the temperature of the living tissue;
compare the calculated time integral value of the temperature of the living tissue with a predetermined setting value for obtaining a predetermined joining strength; and
give an instruction based on a result of the comparison.

2. The living tissue bonding system according to claim 1, wherein the processor is programmed to control the power source so that application of the treatment energy decreases or ends, based on the instruction.

3. The living tissue bonding system according to claim 2, wherein
the sandwiching section applies two or more treatment energies selected a group consisting of heat energy, ultrasound energy, light energy and high frequency power energy to the living tissue; and
the processor is programmed to decrease or terminate output of at least one of the treatment energies based on the instruction.

4. The living tissue bonding system according to claim 1, wherein the processor is programmed to make a notification based on the instruction.

5. The living tissue bonding system according to claim 4, wherein the processor is programmed to:
calculate a ratio of the predetermined setting value to the time integral value of the temperature of the living tissue; and
make a notification of the ratio.

6. The living tissue bonding system according to claim 1, wherein the processor is programmed to set the predetermined setting value, which is to be a target of the time integral value of the temperature of the living tissue.

7. The living tissue bonding system according to claim 6, wherein
the memory is configured to store a plurality of different predetermined setting values.

8. The living tissue bonding system according to claim 7, wherein
the memory is configured to store treatment conditions corresponding to the plurality of different predetermined setting values; and
the processor being programmed to control the power source so that application of the treatment energy decreases or ends based on a selected treatment condition and based on the instruction.

9. The living tissue bonding system according to claim 1, wherein the treatment energy is at least one of heat energy, ultrasound energy, light energy and high frequency power energy.

10. The living tissue bonding system according to claim 1, wherein the sandwiching section comprises a heat generating device for converting the power to heat energy.

11. The living tissue bonding system according to claim 10, wherein the processor is programmed to measure the temperature of the living tissue from an output of the heat generating device.

12. The living tissue bonding system according to claim 1, wherein the processor is programmed to measure the temperature of the living tissue from an output of a temperature sensor.

13. The living tissue bonding system according to claim 1, wherein, when the temperature of the living tissue becomes 50° C. or above, the processor is programmed to start the calculation of the time integral value of the temperature of the living tissue.

14. The living tissue bonding system according to claim 1, wherein the instruction section giving an instruction based on a result of setting an integral of the temperature of the living tissue and a difference between an application start time of the treatment energy and an application end time of the treatment energy as the predetermined setting value and comparing the predetermined setting value with the time integral value.

15. A method for operating a living tissue bonding system, the method comprising:
supplying, to the living tissue, treatment energy for bonding living tissue sandwiched by a sandwiching section;
measuring a temperature of the living tissue sandwiched by the sandwiching section;
calculating, from the measured temperature of the living tissue and a time period of applying the treatment energy, a time integral value of the temperature of the living tissue;
comparing the calculated time integral value with a predetermined setting value; and
giving an instruction based on a result of comparing the calculated time integral value with the predetermined setting value.

16. The method for operating the living tissue bonding system according to claim 15, the method further comprising controlling the power source so that application of the treatment energy decreases or ends, based on the instruction.

17. The method for operating the living tissue bonding system according to claim 16, further comprising:
performing treatment by applying two or more treatment energies selected from a group consisting of heat energy, ultrasound energy, light energy and high frequency power energy to the living tissue; and
when controlling the power source, decreasing or terminating output of the treatment energies based on the instruction of the instruction section.

18. The method for operating the living tissue bonding system according to claim 15, the method further comprising making a notification based on the instruction.

19. The method for operating the living tissue bonding system according to claim 17, wherein:
when comparing the calculated time integral value with the predetermined setting value, calculating a ratio of the predetermined setting value to the calculated time integral value; and
making a notification of the calculated ratio.

20. The method for operating the living tissue bonding system according to claim 15, the method further comprising setting a predetermined setting value which is to be a target of the time integral value of the temperature of the living tissue.

21. The method for operating the living tissue bonding system according to claim 20, the method further comprising storing a plurality of different predetermined setting values.

22. The method for operating the living tissue bonding system according to claim 20, the method further comprising:
storing treatment conditions corresponding to the plurality of different predetermined setting values; and
controlling the power source so that application of the treatment energy decreases or ends based on selected one of the treatment conditions, based on the instruction from the instruction section.

23. The method for operating the living tissue bonding system according to claim 15, further comprising converting power to the treatment energy and treating the living tissue, wherein the power is converted to at least one of heat energy, ultrasound energy, light energy and high frequency power energy and the treatment is performed.

24. The method for operating the living tissue bonding system according to claim 15, further comprising:
converting power to the treatment energy and treating the living tissue; and
converting the power to heat energy.

25. The method for operating the living tissue bonding system according to claim 22, further comprising measuring the temperature of the living tissue based on an output of a heat generating device that is provided on the sandwiching section.

26. The method for operating the living tissue bonding system according to claim 15, wherein, the temperature of the living tissue is measured from an output of a temperature sensor.

27. The method for operating the living tissue bonding system according to claim 15, wherein, the calculation of the time integral value of the temperature of the living tissue starts when the temperature of the living tissue becomes a predetermined lower limit or above.

* * * * *